(12) United States Patent
Orbay et al.

(10) Patent No.: US 7,771,433 B2
(45) Date of Patent: Aug. 10, 2010

(54) BONE FRACTURE FIXATION PLATE SHAPING SYSTEM

(75) Inventors: Jorge L. Orbay, Miami, FL (US); Javier E. Castaneda, Miami, FL (US); Juergen A. Kortenbach, Miami Springs, FL (US)

(73) Assignee: Depuy Products, Inc., Warsaw, IN (US)

( * ) Notice: Subject to any disclaimer, the term of this patent is extended or adjusted under 35 U.S.C. 154(b) by 194 days.

(21) Appl. No.: 11/384,841

(22) Filed: Mar. 20, 2006

(65) Prior Publication Data

US 2006/0161158 A1    Jul. 20, 2006

(51) Int. Cl.
*A61B 17/58* (2006.01)
(52) U.S. Cl. .................. 606/101; 606/86 R; 606/289
(58) Field of Classification Search .............. 606/69, 606/280, 70, 71, 281–285, 290, 101, 104, 606/86 R, 289
See application file for complete search history.

(56) References Cited

U.S. PATENT DOCUMENTS

| 1,105,105 | A |   | 7/1914  | Sherman |
|-----------|---|---|---------|---------|
| 1,326,907 | A |   | 1/1920  | Bond |
| 2,406,832 | A |   | 9/1946  | Hardinge |
| 2,443,363 | A |   | 6/1948  | Townsend |
| 2,494,229 | A | * | 1/1950  | Collison ............ 606/916 |
| 2,500,370 | A |   | 3/1950  | McKibbin |
| 3,289,290 | A |   | 12/1966 | Sandor |
| 3,673,378 | A |   | 6/1972  | Kesling |
| 3,741,205 | A | * | 6/1973  | Markolf et al. ......... 606/291 |
| 3,824,834 | A | * | 7/1974  | Durham ................ 72/387 |
| 3,842,825 | A |   | 10/1974 | Wagner |
| 4,304,117 | A |   | 12/1981 | Rawson |
| 4,364,382 | A |   | 12/1982 | Mennen |
| 4,493,317 | A |   | 1/1985  | Klaue |
| 4,565,193 | A |   | 1/1986  | Streli |
| 4,683,878 | A |   | 8/1987  | Carter |
| 4,740,117 | A |   | 4/1988  | Schaff et al. |
| 4,867,144 | A |   | 9/1989  | Karas et al. |
| 4,889,110 | A |   | 12/1989 | Galline et al. |
| 4,955,886 | A |   | 9/1990  | Pawluk |
| 4,957,497 | A |   | 9/1990  | Hoogland et al. |

(Continued)

FOREIGN PATENT DOCUMENTS

CH            373516         11/1963

(Continued)

OTHER PUBLICATIONS

The Titanium Distal Radius Plate Technique Guide; Synthes, 1996.

(Continued)

*Primary Examiner*—Nicholas D Lucchesi
*Assistant Examiner*—Tara R George
(74) *Attorney, Agent, or Firm*—Gordon & Jacobson, PC

(57) ABSTRACT

Removable guide tips are pre-assembled into threaded holes of a fracture fixation plate. The guide tips may be used with or without drill guides to guide a drill along the axes of threaded holes defined in the plate. In addition, the tips may be used with bending tools to contour the plate laterally, longitudinally and with twist. More particularly, such plate contouring can be performed while the plate is located on the bone.

22 Claims, 9 Drawing Sheets

U.S. PATENT DOCUMENTS

| | | | |
|---|---|---|---|
| 5,002,544 A | 3/1991 | Klaue et al. | |
| 5,015,248 A | 5/1991 | Burstein et al. | |
| 5,022,277 A | 6/1991 | Shaffer | |
| 5,053,036 A | 10/1991 | Perren et al. | |
| 5,139,497 A | 8/1992 | Tilghman et al. | |
| 5,151,103 A | 9/1992 | Tepic et al. | |
| 5,161,404 A | 11/1992 | Hayes | |
| 5,190,544 A | 3/1993 | Chapman et al. | |
| 5,197,966 A | 3/1993 | Sommerkamp | |
| 5,201,737 A | 4/1993 | Leibinger et al. | |
| 5,269,784 A | 12/1993 | Mast | |
| 5,290,288 A | 3/1994 | Vignaud et al. | |
| 5,304,180 A | 4/1994 | Slocum | |
| 5,364,398 A | 11/1994 | Chapman | |
| 5,366,326 A | 11/1994 | Converse | |
| 5,372,598 A | 12/1994 | Luhr et al. | |
| 5,413,577 A | 5/1995 | Pollock | |
| 5,423,826 A * | 6/1995 | Coates et al. | 606/96 |
| 5,474,553 A | 12/1995 | Baumgart | |
| 5,487,743 A | 1/1996 | Laurain et al. | |
| 5,507,801 A | 4/1996 | Gisin et al. | |
| 5,509,933 A | 4/1996 | Davidson et al. | |
| 5,558,674 A | 9/1996 | Heggeness et al. | |
| 5,564,302 A | 10/1996 | Watrous | |
| 5,578,036 A | 11/1996 | Stone et al. | |
| 5,586,985 A | 12/1996 | Putnam et al. | |
| 5,601,553 A | 2/1997 | Trebing et al. | |
| 5,634,927 A | 6/1997 | Houston et al. | |
| D383,841 S * | 9/1997 | Runciman | D24/133 |
| 5,693,055 A | 12/1997 | Zahiri et al. | |
| 5,752,958 A | 5/1998 | Wellisz | |
| 5,779,706 A | 7/1998 | Tschakaloff | |
| 5,785,712 A | 7/1998 | Runciman et al. | |
| 5,851,207 A | 12/1998 | Cesarone | |
| 5,954,722 A | 9/1999 | Bono | |
| 5,993,449 A | 11/1999 | Schlapher et al. | |
| 6,001,099 A | 12/1999 | Huebner | |
| 6,007,535 A | 12/1999 | Rayhack et al. | |
| 6,066,142 A | 5/2000 | Serbousek et al. | |
| 6,077,271 A | 6/2000 | Huebner et al. | |
| 6,129,730 A | 10/2000 | Bono et al. | |
| 6,170,803 B1 * | 1/2001 | Liberfarb | 254/131 |
| 6,235,034 B1 * | 5/2001 | Bray | 606/71 |
| 6,306,139 B1 | 10/2001 | Fuentes | |
| 6,325,803 B1 | 12/2001 | Schumacher et al. | |
| 6,332,887 B1 | 12/2001 | Knox | |
| 6,358,250 B1 | 3/2002 | Orbay | |
| 6,364,882 B1 | 4/2002 | Orbay | |
| 6,416,518 B1 | 7/2002 | DeMayo | |
| 6,436,103 B1 | 8/2002 | Suddaby | |
| 6,506,191 B1 | 1/2003 | Joos | |
| 6,602,255 B1 * | 8/2003 | Campbell et al. | 606/290 |
| 6,623,486 B1 | 9/2003 | Weaver et al. | |
| 6,656,181 B2 | 12/2003 | Dixon et al. | |
| 6,712,818 B1 | 3/2004 | Michelson | |
| 6,730,091 B1 | 5/2004 | Pfefferle et al. | |
| 6,821,278 B2 | 11/2004 | Frigg et al. | |
| 6,928,733 B2 | 8/2005 | Rubbert et al. | |
| 6,960,211 B1 | 11/2005 | Pfefferle et al. | |
| 7,048,477 B2 | 5/2006 | Abrams | |
| 7,189,237 B2 * | 3/2007 | Huebner | 606/69 |
| 7,229,446 B2 | 6/2007 | Capanni | |
| 7,273,481 B2 | 9/2007 | Lombardo et al. | |
| 7,357,804 B2 | 4/2008 | Binder et al. | |
| 7,473,257 B2 | 1/2009 | Knopfle et al. | |
| 2001/0037156 A1 | 11/2001 | Burstein et al. | |
| 2002/0042654 A1 | 4/2002 | Masini | |
| 2003/0083667 A1 | 5/2003 | Ralph et al. | |
| 2003/0171754 A1 | 9/2003 | Del Medico | |
| 2004/0034356 A1 | 2/2004 | LeHuec et al. | |
| 2004/0097937 A1 | 5/2004 | Pike et al. | |
| 2004/0102777 A1 | 5/2004 | Huebner | |
| 2004/0102778 A1 | 5/2004 | Huebner et al. | |
| 2004/0176780 A1 * | 9/2004 | Knopfle et al. | 606/105 |
| 2004/0186482 A1 | 9/2004 | Kolb et al. | |
| 2005/0028398 A1 | 2/2005 | Jacobsen | |
| 2005/0165401 A1 * | 7/2005 | Pack | 606/69 |
| 2005/0182406 A1 | 8/2005 | Orbay et al. | |
| 2005/0187552 A1 | 8/2005 | Michelson | |
| 2005/0234467 A1 * | 10/2005 | Rains | 606/96 |
| 2006/0089648 A1 | 4/2006 | Masine | |
| 2006/0161158 A1 | 7/2006 | Orbay et al. | |

FOREIGN PATENT DOCUMENTS

| | | |
|---|---|---|
| DE | 19936061 | 3/2000 |
| DE | 10015734 | 9/2001 |
| EP | 1836982 | 9/2007 |
| FR | 2 367 479 | 5/1978 |
| JP | 2003 102743 | 4/2003 |
| WO | WO99/05968 | 2/1999 |
| WO | WO 01/91660 | 12/2001 |
| WO | WO/2004/024009 A1 | 3/2004 |
| WO | WO 2004/045455 | 6/2004 |

OTHER PUBLICATIONS

The Distal Radius Plate Instrument and Implant Set Techinque Guide; Synthes; 1995.
SCS/V Distal Radius Plate Volar; Avanta; 1998.
SCS/D Distal Radius Plate System; Avanta; 1997.
Summary of Safety and Effectiveness Information; Synthes (USA); 1996.
Graduated Stability Plates (GSP); Stryker Corporation; 2004.
Hand Innovations, DVR Anatomic Plate with F.A.S.T. Guide Technology, DVR Anatomic The Proven Standard in Volar Plating, on sale as of Mar. 2005.

* cited by examiner

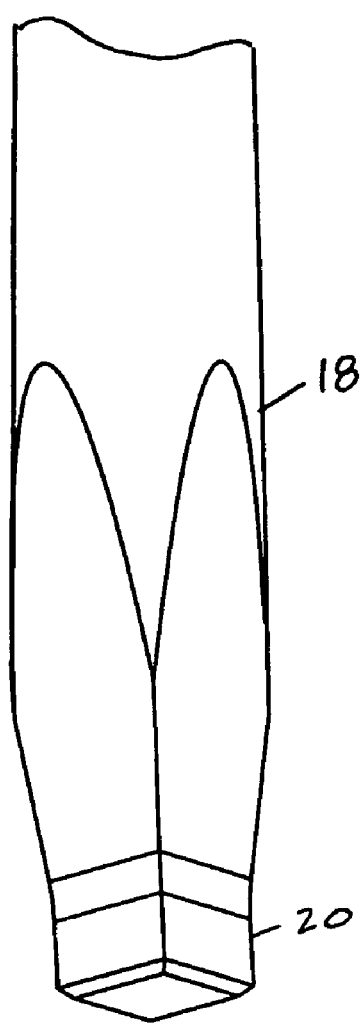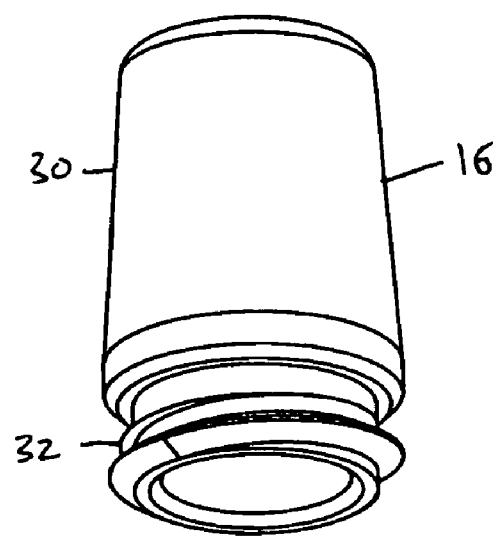
FIG. 2

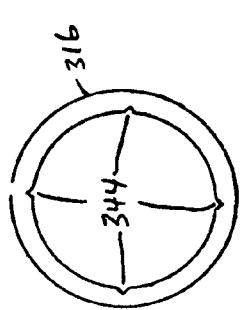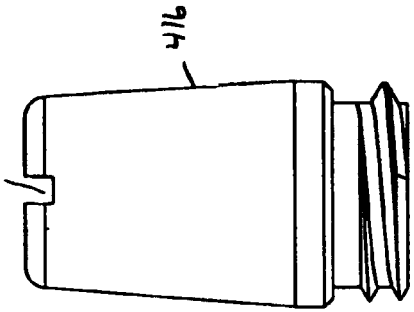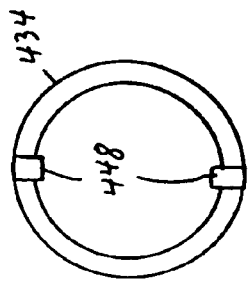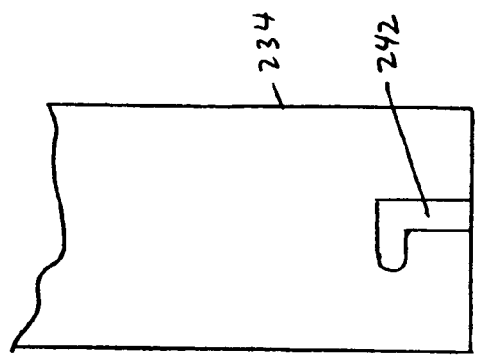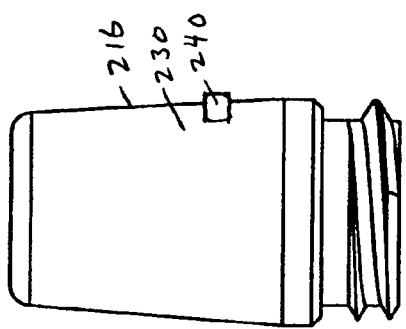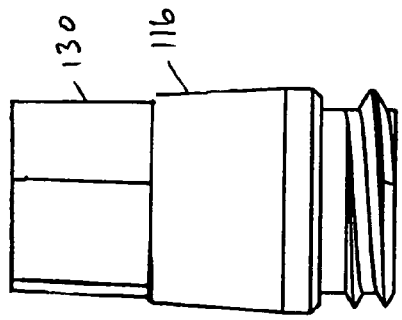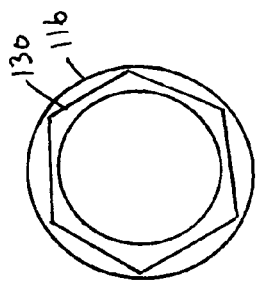

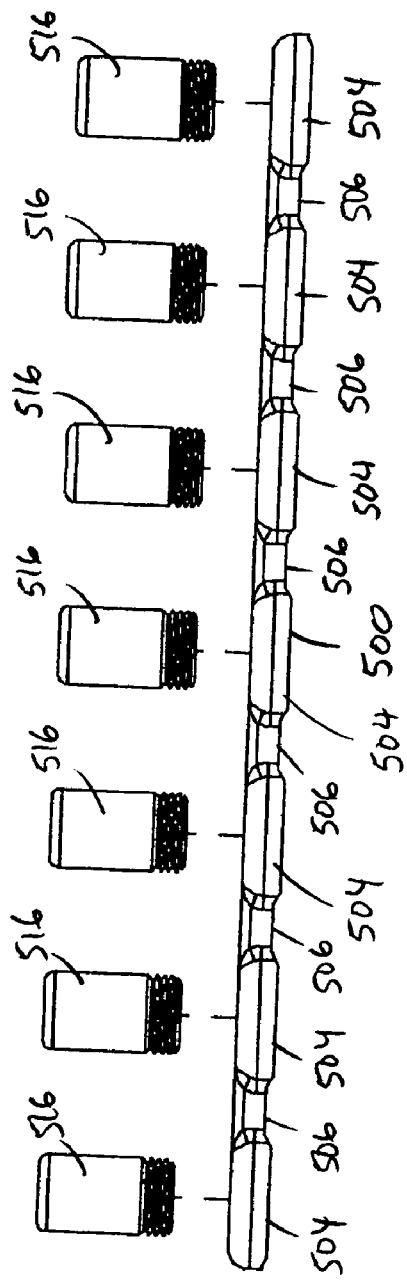
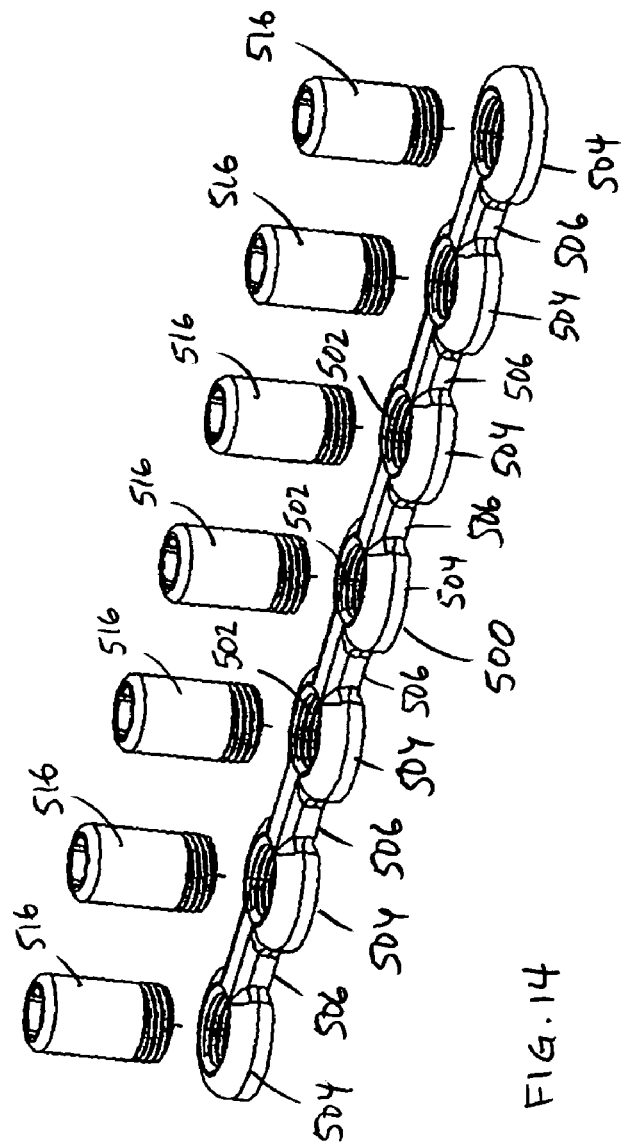
FIG. 13
FIG. 14

BONE FRACTURE FIXATION PLATE SHAPING SYSTEM

BACKGROUND OF THE INVENTION

1. Field of the Invention

This invention relates broadly to surgical devices. More particularly, this invention relates to orthopedic implants, and specifically to elements to implant and shape a bone plate.

2. State of the Art

Fracture to the metaphysis of a long bone can be difficult to treat. Improper treatment can result in deformity and long-term discomfort.

By way of example, a Colles' fracture is a fracture resulting from compressive forces being placed on the distal radius, and which causes backward or dorsal displacement of the distal fragment and radial deviation of the hand at the wrist. Often, a Colles' fracture will result in multiple bone fragments which are movable and out of alignment relative to each other. If not properly treated, such fractures may result in permanent wrist deformity and limited articulation of the wrist. It is therefore important to align the fracture and fixate the bones relative to each other so that proper healing may occur.

Alignment and fixation of a metaphyseal fracture are typically performed by one of several methods: casting, external fixation, pinning, and plating. Casting is non-invasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments. Pinning with K-wires (Kirschner wires) is an invasive procedure whereby pins are positioned into the various fragments. This is a difficult and time consuming procedure that provides limited fixation if the bone is comminuted or osteoporotic.

Plating utilizes a stabilizing metal plate typically placed against the bone, fixed-angle fasteners (which may have threaded or non-threaded shafts) positioned through the plate and entering drilled holes adjacent an articular bone surface, and cortical screws extending from the plate into holes drilled in the bone to provide stabilized fracture fixation. For example, co-owned U.S. Pub. No. 20040193164 A1, which is hereby incorporated by reference herein in its entirety, discloses a plate particularly adapted to treat dorsally displaced metaphyseal fractures from the volar side of the wrist.

When fixed-angle fasteners are utilized in conjunction with a bone plate, it is necessary to ensure that the pilot holes drilled for the fasteners are co-axial with the hole axes. Otherwise, the shaft of the fasteners will not properly align with the anatomy, and the head of the fasteners will not properly align with the threaded holes of the plate, potentially resulting in cross-threading. As a result, with the plate placed upon the bone, prior to drilling each hole in the bone in alignment with a threaded hole, a drill guide is attached to the plate at the threaded hole. The guide defines a tubular passage which directs the drill bit in the proper orientation for a fastener through the particular threaded hole. After drilling each hole, the drill guide is removed, the fastener is inserted in the threaded hole, and the drill guide is coupled to a subsequent threaded hole.

The process of attaching the drill guide during the surgical procedure is laborious. It can be difficult to locate the appropriate angle for threadably coupling the guide to the peg hole during the procedure, given that each threaded hole may have a discrete axis angle from the other threaded holes. Such difficulty can unnecessarily prolong the surgical procedure.

Furthermore, fragment plates are commonly used to fixate fractures along the diaphysis of a bone or at specific diaphyseal-metaphyseal or metaphyseal locations. Such plates are generally elongate, L-shaped, Y-shaped or have another shape which is suited for placement on a portion of a bone. The plates can be of varying length depending upon the intended fixation application. When fragment plates are provided with threaded holes they are subject to the same practical labor intensity for use as presented above with respect to the volar plate; i.e., it is laborious to attach a drill guide at each threaded hole for drilling a hole in alignment with the axis of the hole for receiving the fixed angle fastener therethrough.

In addition, the anatomy for which the fragment plates are designed often differ from the exact contour of the bone contacting surface of the plates. For several reasons it has been impractical to re-contour a fragment plate with threaded holes during the implantation procedure to better fit the anatomy. First, in distinction from non-fixed angle fragment plates, inserting shaping tools into the threaded holes of the plate and applying a force to the plate with the tools will distort the threads making such holes unaccepting to their threaded fasteners. Second, to best fit the anatomy a plate may need to be re-contoured in three dimensions: longitudinal, lateral, and twist. Such modifications are difficult to transfer to a very stiff metal plate, having to place the plate on the bone, remove the bone reshaping, placing the plate back on the bone, making corrections, etc. That is, it is very difficult to reshape any plate to closely fit the bone when such reshaping is done at a distance from the bone.

SUMMARY OF THE INVENTION

It is therefore an object of the invention to facilitate the drilling of holes in bone in alignment with the threaded holes in a bone plate.

It is another object of the invention to obviate the difficulties presented in connecting a drill guide in alignment with a threaded fixed angle hole in a bone plate at the time of surgery.

It is also an object of the invention to provide a system to reshape a plate while the plate is located on the bone.

It is a further object of the invention to protect a system which permits reshaping of the plate in three dimensions.

It is yet another object of the invention to provide a system which protects the threads of fixed angle holes during plate reshaping.

In accord with these objects, which will be discussed in detail below, drill guide tips are pre-assembled into at least one and preferably each of the threaded holes of the plate, so that surgeon does not have to thread the drill guide with the plate positioned on the bone. The pre-assembly can be done by the operating room technician or at the factory. The drill guide tips may be reusable or disposable. The tips are sufficiently short enough so that they do not interfere with adjacent tips or adjacent structure on the plate or intended to be inserted through the plate.

In a preferred method of pre-assembling the tips to the plate, a nest of short pins is placed beneath the plate such that the pins extend through the holes in the plate along the same angles as the axes of the holes. The pins then guide the tips to be thread into the holes at the correct angle. Alternatively, no nest is utilized and the tips are individually guided into the holes at the appropriate angle. With respect to a fragment plate, such angle is typically normal to the bone contacting surface of the plate.

There are two options for using the tips as drill guides. One is to attach a drill guide extension. The tip and extension together function as a conventional drill guide. After drilling, the extension is used to remove the tip from the plate. According to another use, the tip is used as a guide for a drill bit without any additional extension and then removed with a separate tool.

In addition, the guide tips have purpose other than for guiding a drill. The guide tips can also be used in conjunction with plate bending tools, and are particularly advantageous when the guide tips are pre-assembled on a fragment plate having a plurality of spaced apart fixed angle holes separated by a plate portion which can be deformed under force. Preferably two tools are used together to bend the plate, and the bending tools have first and second ends which are at least partially inserted into guide tips in two adjacent holes in the plate. Torque is applied by coupling the first ends of each of the tools to the guide tips inserted in threaded holes and manipulating the tools, lateral bending forces (i.e., bending within the plane of the plate) are applied with the second ends in the guide tips, and longitudinal bending forces are applied with the first ends or a combination of the first and second ends in the guide tips. The bending tools can be operated and forces can be applied to reshape the plate with the plate positioned directly on the bone to reshape the plate in close conformance to the bone surface. As the plate is shaped at each set of two holes, bending tools are removed and the guide tips can be used as discussed above as drill guides to drill holes into bone beneath that portion of the plate. Fixed angle screws are then used to couple that portion of the fragment plate to the bone. The adjacent portion of the plate is then shaped and fixed to the bone in a like manner with the process repeated until the entire plate is shaped and coupled to the bone.

Additional objects and advantages of the invention will become apparent to those skilled in the art upon reference to the detailed description taken in conjunction with the provided figures.

BRIEF DESCRIPTION OF THE DRAWINGS

FIG. 2 is an exploded perspective view of drill guide tip and tool;

FIG. 6 is a side elevation of a first embodiment of a drill guide tip;

FIG. 7 is a top view of the first embodiment of the drill guide tip;

FIG. 8 is a side elevation of a second embodiment of a drill guide tip;

FIG. 9 is a side elevation view of an embodiment of drill guide extension;

FIG. 10 is a top view of a third embodiment of a drill guide tip;

FIG. 11 is a side elevation of a fourth embodiment of a drill guide tip;

FIG. 12 is a bottom view of an embodiment of a drill guide extension engageable with the drill guide tip of FIG. 11;

FIG. 13 is an exploded side elevation view of a fragment plate with guide tips;

FIG. 14 is an exploded perspective view of the fragment plate and guide tips of FIG. 13;

DETAILED DESCRIPTION

Figure 1:
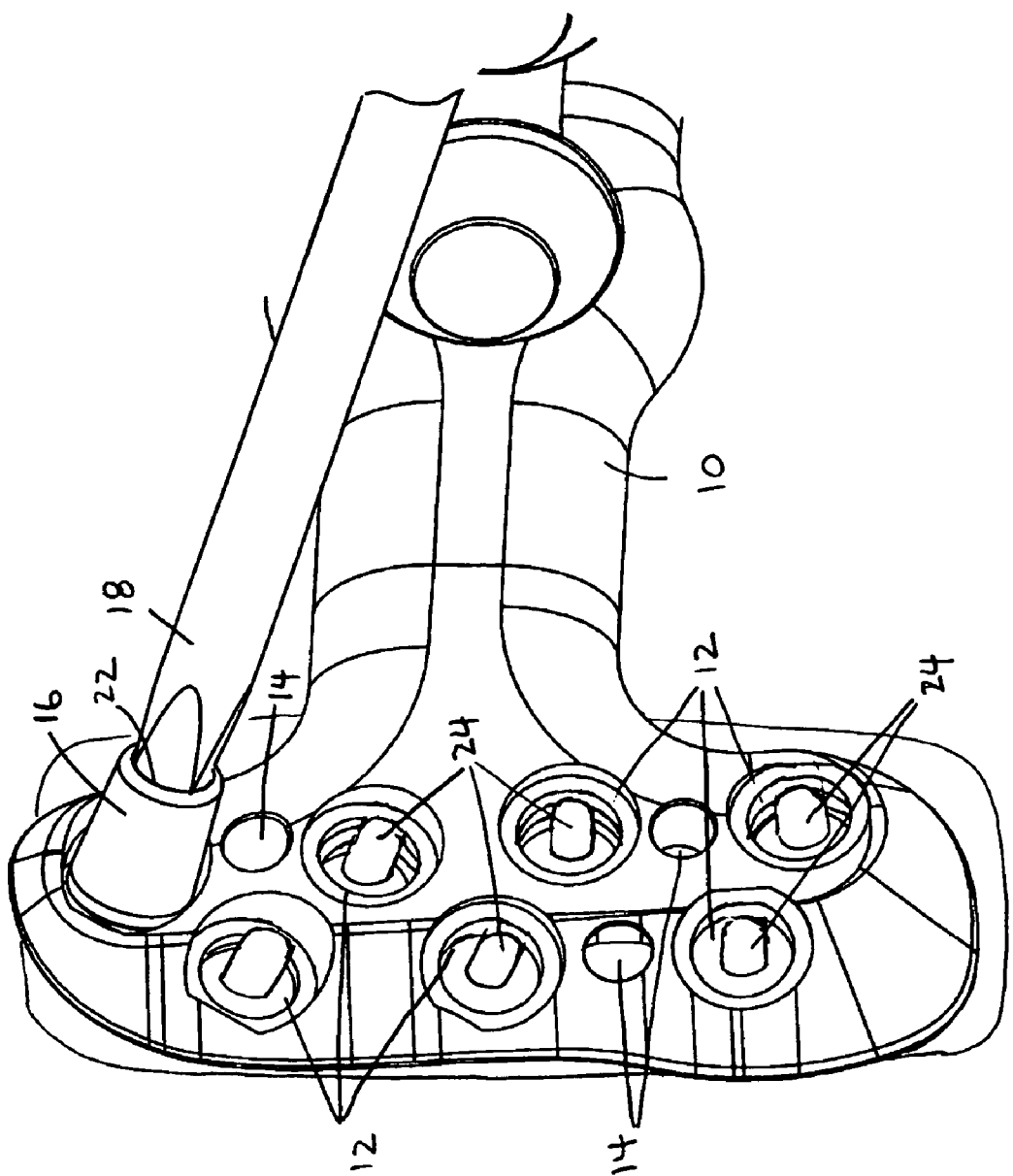
FIG. 1 is a perspective view of a bone plate and a drill guide tip being inserted or removed from the plate with a tool.

Turning now to FIG. 1, a bone plate 10 is shown. The bone plate shown is particularly for placement over the volar side of the distal radius. The bone plate 10 includes a plurality of threaded peg holes 12 for threadably receiving the heads of pegs or locking screws (not shown) therein and relatively smaller alignment holes 14 sized to closely receive K-wires in a fixed angle orientation. In a preferred bone plate, the axes of the peg holes are all oblique relative to each other. In one of the peg holes, a drill guide tip 16 is shown being pre-assembled into the hole with an insertion tool 18. Referring to FIGS. 1 and 2, in a preferred embodiment, the engagement between the insertion tool 18 and tip 16 is a tapered square 20 engaging a circular opening 22, with the edges of the square driver providing sufficient frictional force to rotate the tip into and out of engagement with the plate 10. Other suitable engagements may be used as well.

Pre-assembly of the tips 16 into the peg holes of the plate 10 is preferably performed so that surgeon does not have to thread the drill guide tips 16 with the plate once the plate 10 is positioned on the bone during the procedure. The pre-assembly can be done by the operating room technician or at the factory. In a preferred method of pre-assembly, a nest of short pins 24 is placed beneath the plate such that the pins extend through the holes in the plate along the same angles as the axes of the holes. The pins 24 then guide the tips to be thread into the holes at the correct angle. With respect to a fragment plate, such angle is typically normal to the bone contacting surface of the plate. The pins 24 and insertion tool 18 are sized such that they do not interfere with each other. Alternatively, no nest is utilized and the tips 16 are individually guided into the holes at the appropriate angle. The drill guide tips 16 may be reusable or disposable.

Figure 3:
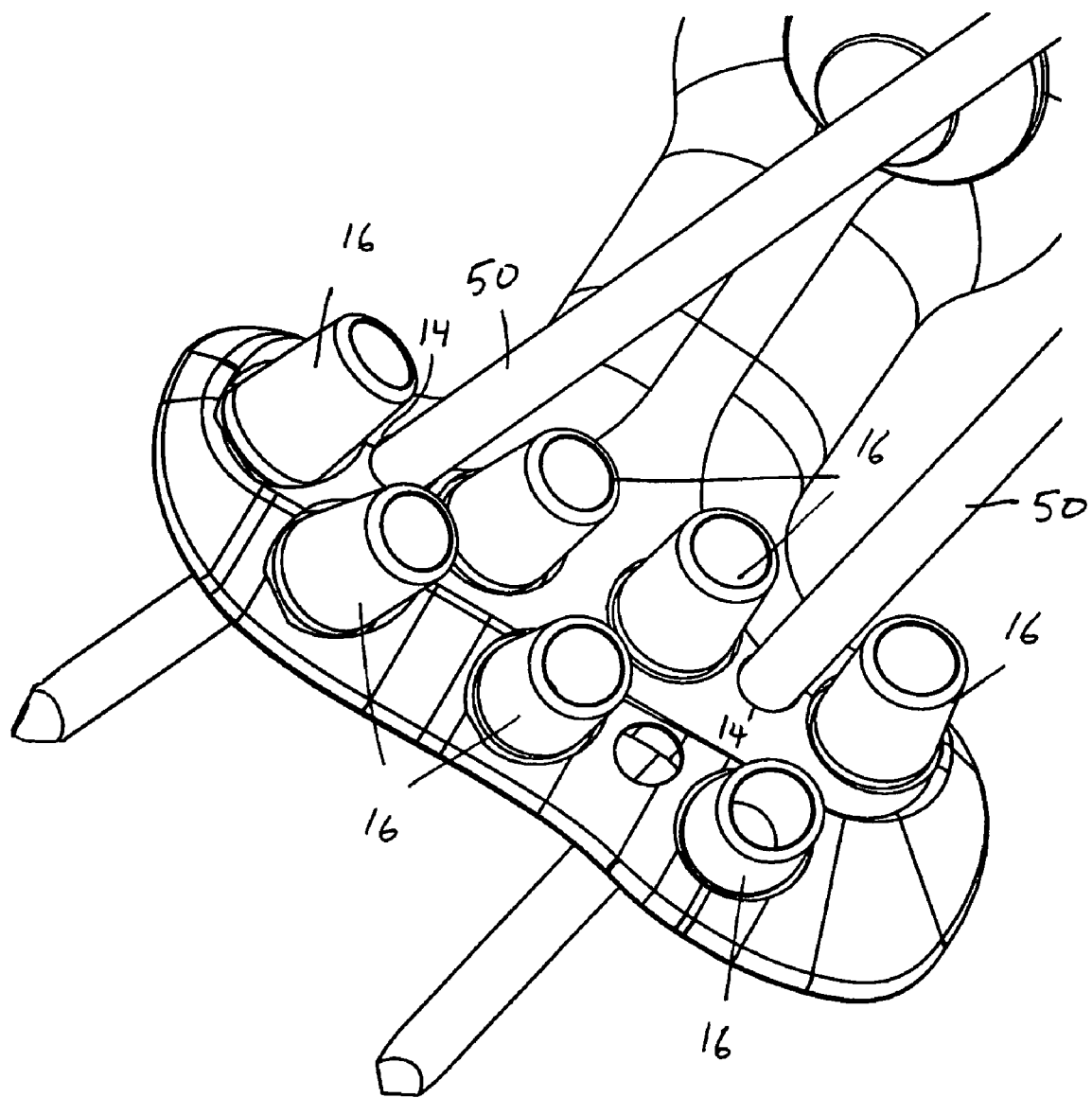
FIG. 3 is a perspective view of the bone plate loaded with drill guide tips and K-wires.

Referring to FIGS. 2 and 3, the tips 16 have a frustoconically tapered upper portion 30 and lower threaded portion 32, and are sufficiently short so that they do not interfere with adjacent tips, adjacent structure on the plate, or structure intended to be inserted through the plate, e.g., K-wires 50 through alignment holes 14. Alternatively, the upper portion 30 may be cylindrical. The lower threaded portion 32 of the tips do not have to be as long as conventional drill guides, as the threading into the plate is done away from the surgical environment under easier conditions, whether at the factory (best case) or pre-implantation at the medical facility. Shortening the threaded portion reduces protrusion of the guide tip below the plate relative to convention drill guides, allowing the plate 10 to sit closer to the bone while drilling, as discussed further below.

The drill guide tips also eliminate the need to "countersink" holes for a drill guide for the distal row of holes in a distal radius plate. More particularly and for the following reasons, in the prior art it is initially necessary to drill holes in bone through the distal row of threaded peg holes with a drill bit larger than the diameter of the peg shaft which will eventually be inserted through the peg holes. The plate is very thin at the distal row. The prior art drill guide has a "nose" section which is cylindrical and unthreaded and approximately 0.030" long, which is slightly longer than the pitch of the peg-hole thread (0.023"). The nose section diameter is just under the inner diameter of thread so that it guides itself with one full turn of the thread and establishes the direction of the hole before the threads are engaged. If the plate thread depth is very small (as is the case for distal holes) there is no room below the plate for the nose section of the drill guide because the bone block entry. Thus, countersink holes must be drilled.

Figure 4:
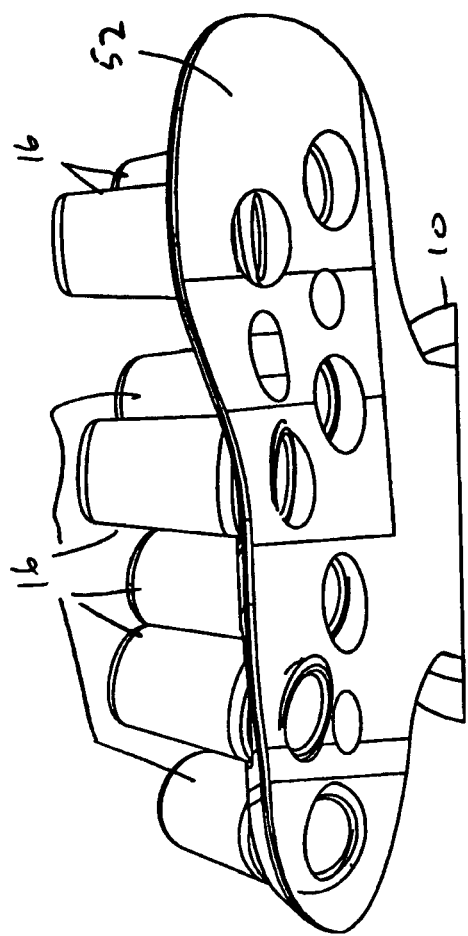
FIG. 4 is a front end view of a head portion of the plate showing that the drill guide tips do not protrude through the bottom surface of the plate.

In accord with the invention, the drill guide tips do not require a "nose" section since they will be assembled with some other guidance (e.g., the above described nest of pins 24) or freehand. The drill guide tips can be made very short since they need just to hold on to the threads of the peg holes of a distal radius plate. One and half threads of engagement has been shown to provide a satisfactory coupling of the tip to the plate, and referring to FIG. 4 provides that the drill guide tip 16 does not protrude through the bottom 52 of the plate 10. In addition to eliminating the requirement for countersinking, the fact that drill guide tips are so short results in the plate seating almost completely flush on the bone. Furthermore, the cylindrical unthreaded nose portion of the conventional drill guide, whose only job is to help the surgeon find by feel the current angle of the peg hole, is not required. A preferred size for each tip is preferably approximately 0.150-0.250 inch in length and certainly less than one inch. As such tip rises a short distance (maximum one inch and preferably not more than 0.25 inch) above the upper surface (the surface opposite the bone contacting surface) of the plate.

There are two options for using the tips as drill guides. According to a first option, the tips 16 are used as the sole guide for a drill bit and then removed with a tool similar to the insertion tool 18. The length of the tips provide sufficient guidance for the drill bit. In this use, the inner surface of the tip is preferably hard, e.g., metal. Thus, the tips 16 may be made entirely of metal or have an outer plastic body with an insert molded metal tube, e.g. hypotube, which is hard and readily available with thin walls.

Figure 5:
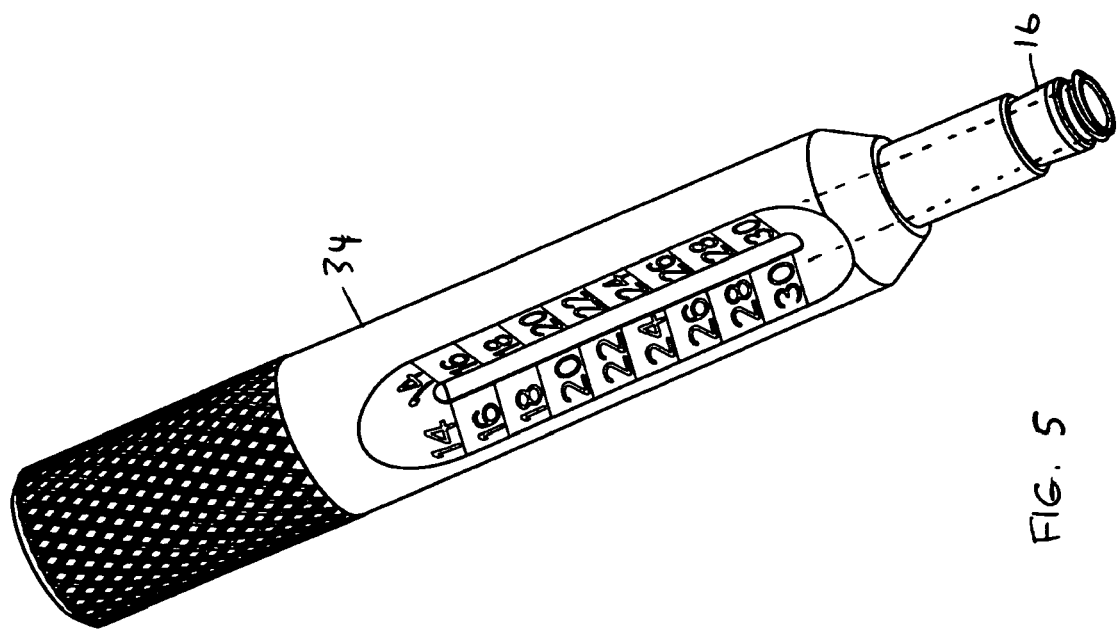
FIG. 5 is a perspective view of a drill guide tip and drill guide extension.

Referring to FIG. 5 and according to a second option, a drill guide extension 34 may be attached to the top of the tip 16. The tip 16 and extension 34 together function as a full length drill guide. The engagement between the drill guide extension 34 over the tip 16 is preferably such that a continuous constant diameter path is provided through the interiors of the extension and tip. To that end, the end 36 of the extension 34 is preferably stepped to fit the upper portion of the tip. The surgeon drills through the drill guide extension and tip, thereby taking advantage of the longer guidance which may be used in conjunction with a scale and/or gauge to measure the depth of the drilled hole for peg length selection. After drilling, the extension 34 and tip 16 are removed from the plate 10, and the extension 34 may also function as a tool for tip 16 removal. In fact, the taper at the upper portion 30 of the tip provides a means for axial and frictional engagement by the extension 34 which permits rotational engagement. Once removed from the plate, the tip is then is pulled of the extension by hand or may be dispensed into a container without manual contact.

It is desirable to have some provision within the surgical set to collect the tips for counting as they are removed; i.e., to ensure that all tips from the plate are removed from the surgical site. In order to facilitate collection of the tips, it is desirable that the drill guide tips have a very conspicuous color, e.g., green or blue. If made out of metal, it may be desirable to make them out titanium or aluminum and anodize them in a bright color that contrasts with the background in the surgical wound and the bone plate. A specialized container may be provided, or a dummy plate with threaded holes may be used to attach the tip thereto.

For drilling through the tips 16 where no drill guide extension is used, it may be desirable to modify the flutes of the drill bit, e.g. shortening and/or increasing twist, to reduce the play within the tip.

Other embodiments of the tips and extensions may be provided. For example, referring to FIGS. 6 and 7, the tips 116 may have an upper portion 130 with a exterior hex shape, or any non-circular exterior cross-sectional shape that will facilitate torque transmission. To remove the tip from the plate the surgeon rotates the extension, unthreading the tip.

Turning now to FIGS. 8 and 9, according to another embodiment of the invention, the tips 216 may be joined to the extension via one or more lateral protrusions 240 on the body 230 of the tip and corresponding "key slots" 242 in the extension 234.

Referring to FIG. 10, according to a further embodiment of the invention, the tips 316 may be joined to the extension by providing one or more corners 344 to the inner circular opening 322 of the tip, and one or more outer corresponding corners on the extension which frictionally engage in the tip.

Turning to FIGS. 11 and 12, according to another embodiment of the invention, the tips 416 may include an upper radially arranged slots 446 (e.g., 180° or 120° separation) and the extension 434 includes corresponding radially arranged pegs 448 which engage the tips 416 at the slots 46.

Turning to FIGS. 13 and 14, the tips can also be used in the bending of a fragment plate 500 in manner that does not distort the threads at the holes 502 at which the tips 516 are coupled, as described below. The tips 516 are cylindrical having inside corners 544 to aid removal and/or extension guide coupling. Such distortion would otherwise prevent the holes 502 from accepting fixed angle fasteners with threaded heads which are later threadably coupled into the threaded holes. The fragment plate 500 is preferably designed with a series of alternating round portions 504 and relatively narrower bridge portions 506 which connect the round portions, and the threaded holes 502 are provided in the round portions. Preferably each threaded hole is provided with a guide tip 516, however the tips may be strategically pre-assembled at locations that are recognized to commonly benefit from contour shaping for the plate 500 depending on the shape of the plate and to best fit on the bone.

Figure 15:
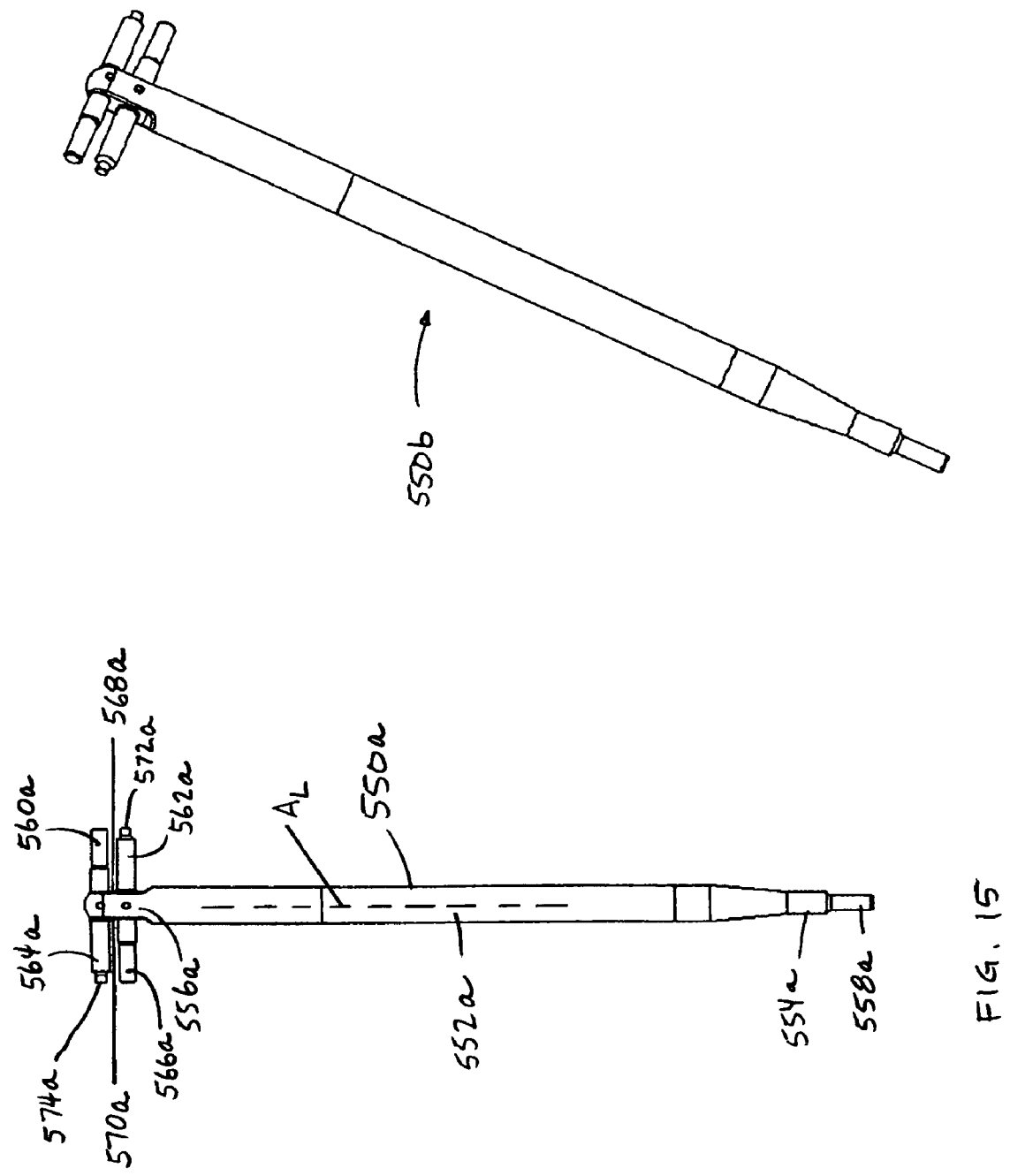
FIG. 15 is a set of shaping tools, shown in side elevation and perspective view.

Referring to FIG. 15, two preferably identical shaping tools 550a, 550b have ends which can be coupled to the tips 516 and are used together to contour the plate 500 (FIGS. 13 and 14). As described in more detail below, the tools 550a, 550b and tips 516 permit such plate contouring to occur with the plate 500 positioned directly on the bone. Each tool, described with respect to tool 550a, includes a handle portion 552a and first and second ends 554a, 556a which can be at least partially inserted into the guide tips 516. The first end 554a includes a preferably axially directed (or preferably at least directed generally parallel to the longitudinal axis $A_L$ of the handle portion 552a) peg element 558a which closely corresponds in size to the inner diameter of a guide tip 516. The second end 556a is provide with four peg elements 560a, 562a, 564a, 566a, with two such pegs extending transversely to the longitudinal axis $A_L$ of the handle on each side 568a, 570a of the second end 556a. At one such side 568a, the endmost peg element 560a closely corresponds in size to the inner diameter of a guide tip 516 and the inner peg element 562a has a stepped down nipple portion 572a, whereas on the opposite side 570a of the second end the endmost peg element 564a has a stepped down nipple portion 574a stepped down in diameter and the inner peg element 566a closely corresponds in size to the interior of the guide tip 516. All the peg elements are preferably generally cylindrical, but may be polygonal or slightly tapered.

As described as follows, the shaping tools 550a, 550b can be coupled to a fragment plate at the guide tips 516 to apply torque, lateral and longitudinal bending forces to contour the plate. It is preferred that the shaping tools be coupled at adjacent guide tips for localized control of plate shaping. The plate is then shaped through a series of shaping steps in which adjacent portions of the plate are sequentially shaped, as needed. Additionally all such shaping, as also discussed further below, can be performed while the plate is positioned on the bone.

Figure 16:
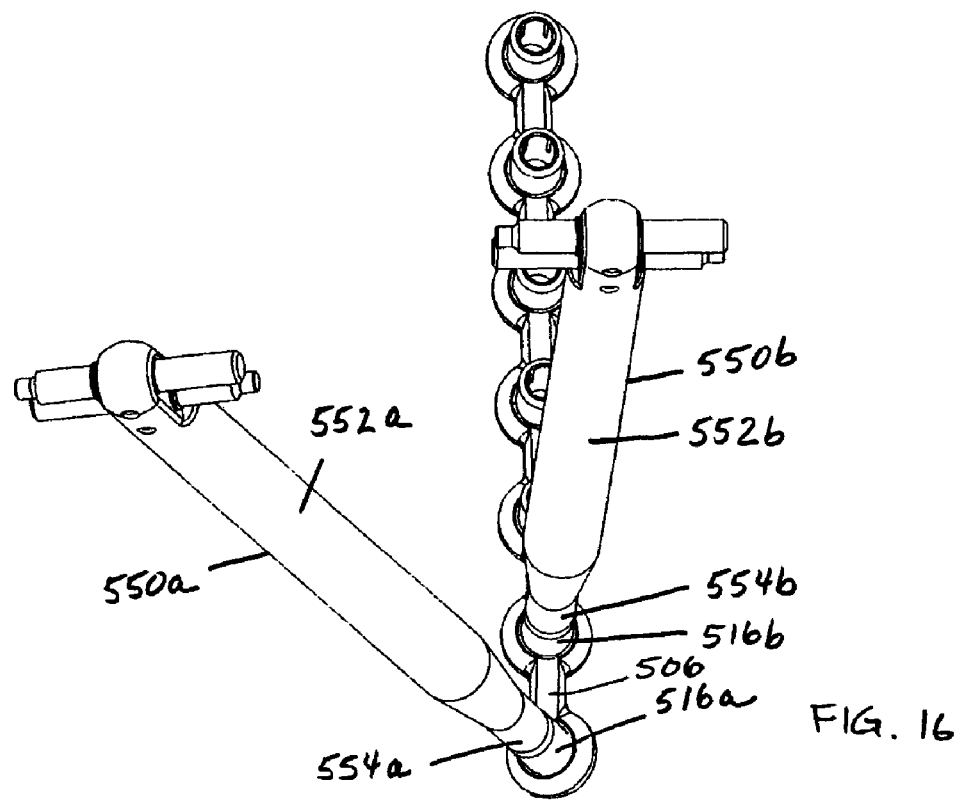
FIG. 16 is a top perspective view of the shaping tools imparting a twist to the fragment plate.

Referring to FIG. 16, in order to apply torque to the plate to cause the plate to twist, the peg elements 558a, 558b (FIG. 15) at the first ends 554a, 554b of the tools 550a, 550b are inserted into preferably adjacent guide tips 516a, 516b. The handle portions 552a, 552b of the tools are then forced laterally relative to each other so as to apply a torque along the bridge portion 506 of the plate between the tools. Such torque results in defining a twist in the plate without deformation to the threaded holes.

Figure 17:
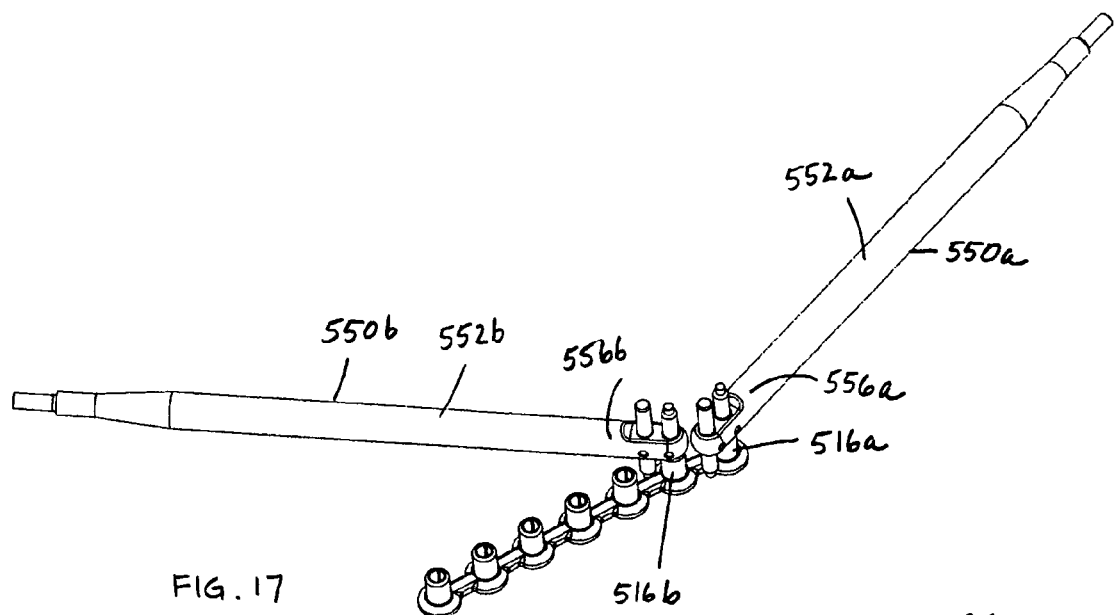
FIG. 17 is a perspective view of the shaping tools imparting a lateral bend to the fragment plate.
Figure 18:
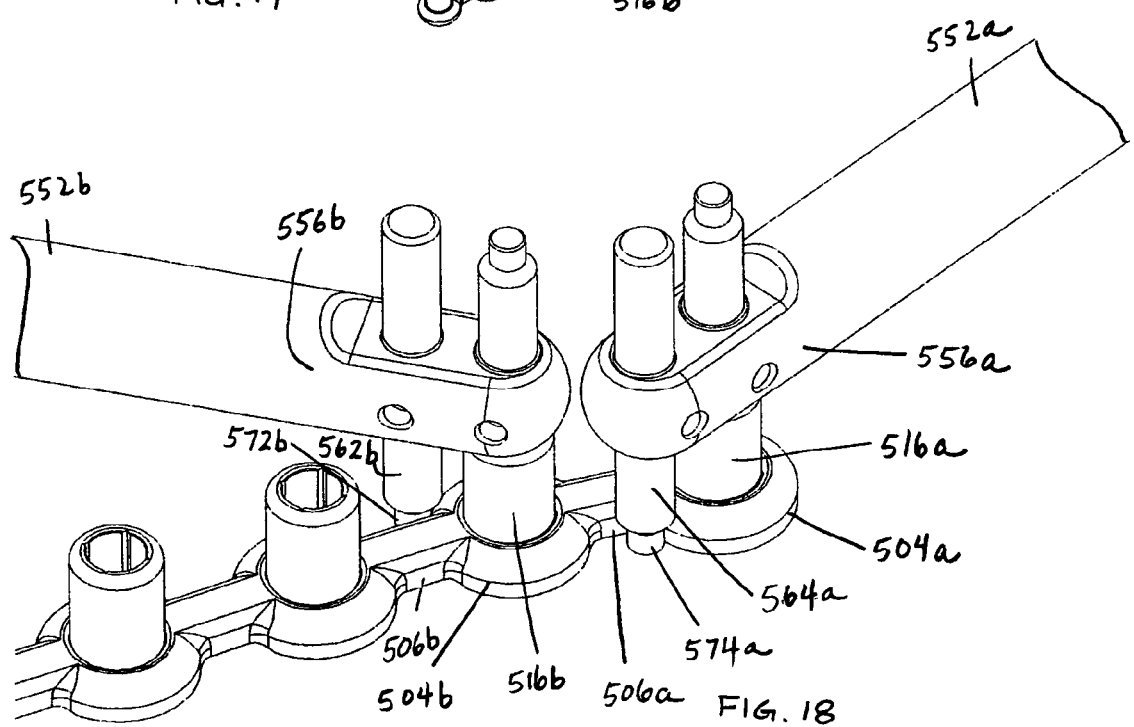
FIG. 18 is an enlarged view similar to FIG. 17.

Referring to FIGS. 17 and 18, lateral bending forces (i.e., bending within the plane of the plate) are applied with the second end 556a, 556b of the shaping tools 550a, 550b coupled to the guide tips 516a, 516b, and then manipulating the shaping tools. Referring to FIG. 18, more particularly, on shaping tool 550a, peg elements 566a (not shown, see FIG. 15) is inserted into guide tip 516a and the nipple portion 574a of peg element 564a functions as rotational stop against the bridge portion 506a of the plate to transfer rotational forces applied by the handle portion 552a of shaping tool 550a. On shaping tool 550b, peg element 560b (not shown, see FIG. 15) is inserted into guide tip 516b and the nipple portion 572b of peg element 562b functions as rotational stop against the bridge portion 506b of the plate to transfer rotational forces applied by the handle portion 552b of shaping tool 550b. As shaping tools 550a, 550b are operated together, the resulting force subjects the plate to lateral bending at the bridge portion 506a located between the plate portions 504a, 504b at which the guide tips are coupled.

Figure 19:
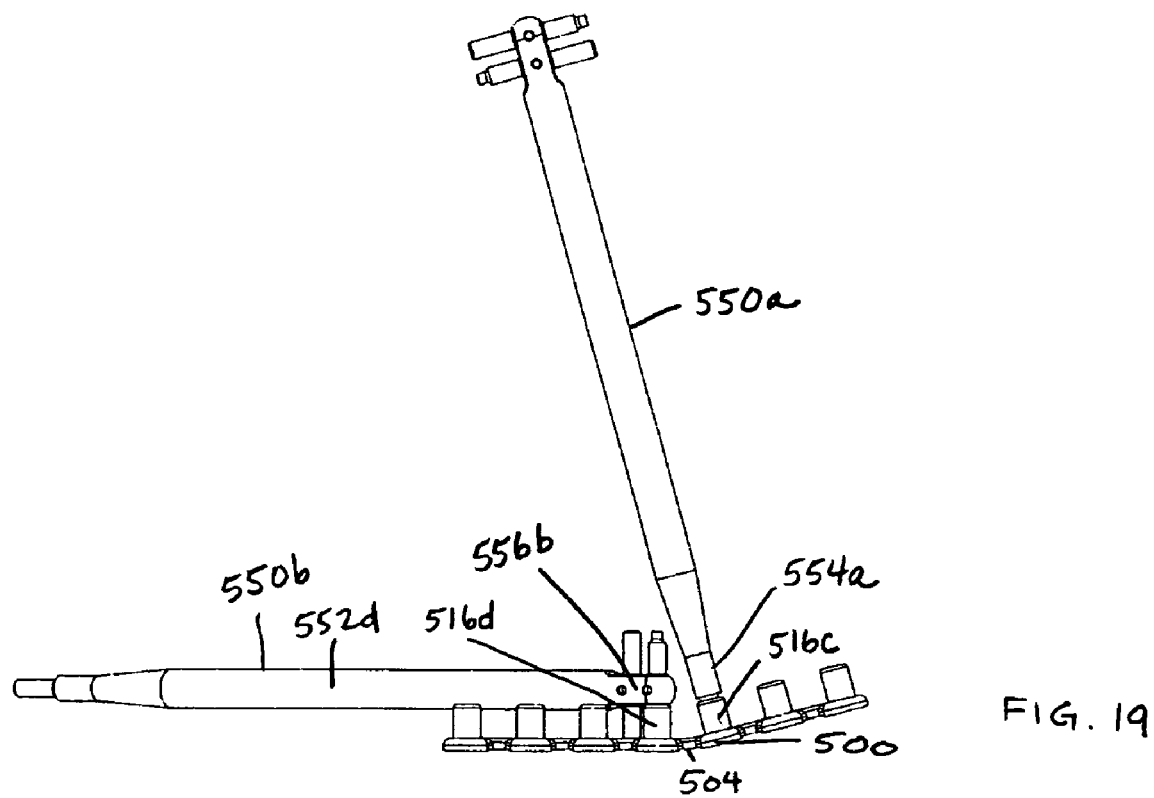
FIG. 19 is a side elevation view of the shaping tools imparting a longitudinal bend to the fragment plate.

Referring to FIG. 19, longitudinal bending forces are applied by inserting the peg element at the first end 554a of shaping tool 550a into guide tip 516c and a peg element, e.g., peg element 560b, at the first 554b or second end 556b (shown) of second shaping tool 550b into guide tip 516d. With the second end 556b coupled at guide tip 516d, the handle portion 552b thereof can be stabilized relative to the bone. The handle portion of tool 550a is then manipulated to bend the plate 500 at the bridge portion 504 between the two tools.

Because the shaping tools are not coupled at any locations below the surface of the plate nor do they have any portion which would otherwise interfere with the bone or bone contacting surface, plate shaping can occur directly on the bone. In one method of operation, a hole is first drilled through a guide tip at an end of the plate. The guide tip is then removed and a threaded fastener is inserted through the threaded hole of the fragment plate and into the drilled hole to couple the plate to the bone. The shaping tools are then worked along the plate, moving hole by hole away from the first coupled hole to shape the plate to the bone as described above. As the plate is shaped at each hole, a hole is drilled through the respective guide tip, the guide tip is removed and a threaded fastener is inserted to hold the plate to the bone. The tools are then moved to a subsequent set of holes along the plate for shaping until the plate is fully contoured and coupled to the bone. In another method, after the plate is coupled to the bone at an end, the plate is shaped along its entire length prior to coupling to the bone at remaining holes. In yet another embodiment, the plate may be shaped to the bone before it is attached at any screw hole. It is recognized that other variations on shaping and coupling can be used.

There have been described and illustrated herein several embodiments of a bone plate with pre-assembled guide tips, tools for use with a plate with guide tips, and methods of using the same. While particular embodiments of the invention have been described, it is not intended that the invention be limited thereto, as it is intended that the invention be as broad in scope as the art will allow and that the specification be read likewise. Thus, while the tips and shaping tools have been shown with respect to a volar plate for dorsally displaced fractures and a straight elongate fragment plate, it will be appreciated that the tips may be used in conjunction with threaded holes on other bone plates as well. For example, the tips may be used in conjunction with any plate for which they would provide advantage. In addition, the shaping tools may be used to customize a fracture fixation plate for other bones, e.g., the clavicle, the ulna, the olecranon, the jaw, the skull, whether such plates are pre-formed flat or contoured to fit the anatomy. Furthermore, a distal radius plate having radial and ulnar sides provided with threaded fixed angle holes, the radial and/or ulnar sides being provided with guide tips and being shapeable with the shaping tools, is considered within the scope of the invention. Also, a distal radius plate having shapeable segment(s) for capturing a volar marginal fragment is also within the scope of the invention. Optionally, such shapeable segment(s) may be removable from the plate if not used, e.g., by repeated bending, and provide a relatively clean break with the plate. In addition, while particular engagements between the tips and the insertion/removal tool and the tips and drill guide extension have been disclosed, it will be understood that other suitable engagements, including non-destructive press-fit, snap-in, bayonet lock, etc. can also be used. Also, while the guide tips are described as threaded into the threaded holes, it is appreciated that non-threaded assemblies, including non-destructive press-fit, snap-in, bayonet lock, etc., which maintain the tips in alignment with the axes of the peg holes can also be used. With respect to the shaping tools, preferred orientations of the peg elements have been described, but other configurations are possible within the scope of the invention. For example, the four peg elements can be located two each at, e.g., 90° apart. In addition, each shaping tool may only have two peg elements at its second end, each with a different configuration of larger and smaller size peg elements. Furthermore, while it is preferred to work a plate for shaping by coupling the shaping tools at guide tips at adjacent holes, it is appreciated that not all holes of a shapeable plate need be provided with a guide tip and that the shaping tools may be used relatively more spaced apart along the plate regardless of whether all holes of a shapeable plate includes guide tips. It will therefore be appreciated by those skilled in the art that yet other modifications could be made to the provided invention without deviating from its scope.

What is claimed is:

1. A fracture fixation plate shaping system, comprising:
   a) a bone plate including a plurality of longitudinally displaced threaded holes;

b) a plurality of removable tubular elements removably coupled in said threaded holes;

c) a first shaping tool having a handle portion having a first portion and an end portion sized and shaped to engage with one of said tubular elements, said first and end portions located at opposite ends of said first shaping tool and transversely oriented relative to each other; and d) a second shaping tool having a handle portion having a first and an end portion sized and shaped to engage with another of said tubular elements, said first and end portions located at opposite ends of said second shaping tool, said first and second shaping tools longitudinally engageable with said tubular elements for the manual application of force to said bone plate to bend said bone plate relative to three axes between two adjacent threaded holes in which said tubular elements are removably coupled.

2. A system according to claim 1, wherein:
said plate has a bone contacting surface and an opposite surface, and
each of said tubular elements has a first end which is coupled to said plate and an end opposite said first end which is located not more than approximately 0.25 inch from said opposite surface of said bone plate.

3. A system according to claim 2, wherein:
said first end of each of said tubular elements is a threaded end.

4. A system according to claim 1, wherein:
said tubular elements having an inner diameter, and
said end portion of each of said first and second shaping tools include a portion which closely corresponds in size to the inner diameter for insertion therein.

5. A system according to claim 1, wherein:
said end portion of at least one of said shaping tools includes a cylindrical peg extending parallel to a longitudinal axis of said shaping tool, said peg having a diameter which closely corresponds in size to an inner diameter of the tubular elements.

6. A system according to claim 1, wherein:
said end portion includes two parallel spaced apart peg elements, at least one of which closely corresponds in size to an inner diameter of the tubular elements.

7. A system according to claim 6, wherein:
one of said pegs is stepped in diameter.

8. A system according to claim 7, wherein:
said peg stepped in diameter is spaced closer to an end of said end portion.

9. A system according to claim 7, wherein:
said peg stepped in diameter is spaced further from an end of said end portion.

10. A system according to claim 6, wherein:
said end portion includes four pegs arranged in first and second sets of two, in said first set one of said pegs is stepped in diameter and spaced closer to an end of said end portion, and in said second set one of said pegs is stepped in diameter and spaced further from said end of said end portion.

11. A system according to claim 10, wherein:
said four pegs are parallel.

12. A system according to claim 6, wherein:
said proximal portion of first shaping tool includes a peg extending parallel to a longitudinal axis of said first shaping tool.

13. A system according to claim 1, wherein:
said first portion of said first shaping tool includes structure sized and shaped to engage a tubular element.

14. A system according to claim 13, wherein:
said first portion of said first shaping tool also includes structure to engage the said bone plate.

15. A system according to claim 14, wherein:
said first portion of said second shaping tool includes structure sized and shaped to engage a tubular element.

16. A system according to claim 15, wherein:
said first portion of said first shaping tool also includes structure to engage the said bone plate.

17. A system according to claim 1, wherein:
said first portion of said first shaping tool includes first structure sized and shaped to engage a first tubular element and second structure sized and shaped to engage an exterior portion of said plate, said first and second structure being different in shape from each other, and
said first portion of said second shaping tool includes third structure sized and shaped to engage a second tubular element and fourth structure sized and shaped to engage an exterior portion of said plate, said third and fourth structure being different in shape from each other.

18. A system according to claim 17, wherein:
said first and third structures are cylindrical and have a free end with a first diameter, and said second and first structure are cylindrical and a free end with a second diameter different from said first diameter.

19. A shaping tool for bending a fracture fixation plate, comprising:
a) a rigid manually leveragable handle portion defining a longitudinal axis;
b) a first end having a first peg element with a first diameter, the first peg element projecting relative to the handle so as to be capable of applying a bending force relative to the plate; and
c) a second end having second and third parallel spaced apart peg elements longitudinally displaced along said longitudinal axis, said second and third peg element fixed relative to each other, said second peg element having a diameter the same as said first diameter, said third peg element stepped in diameter to have an end portion smaller in diameter than said first diameter, and said second and third peg elements being oriented at an angle transverse to said first peg element,
wherein said handle is located between said first and second ends.

20. A shaping tool according to claim 19, wherein:
said third peg element is spaced closer to an end of said end portion than said second peg element.

21. A shaping tool according to claim 20, wherein:
said second end portion includes fourth and fifth peg elements, with the fourth peg element having a diameter substantially the same as said first diameter and the fifth peg element having a stepped diameter with a reduced diameter at its end,
said second and third peg elements being located on one side of said second end portion and said fourth and fifth peg elements being rotatably displaced relative to the second and third peg elements,
said fifth peg element being spaced further from said end of said second end portion than said fourth peg element.

22. A shaping tool according to claim 19, wherein:
said third peg element is spaced further from an end of said end portion than said second peg element.

* * * * *